United States Patent [19]

Hickner

[11] 4,104,283

[45] Aug. 1, 1978

[54] POLYTHIOETHERALKYLENEOXIDE EPOXIDES

[75] Inventor: Richard A. Hickner, Midland, Mich.

[73] Assignee: The Dow Chemical Company, Midland, Mich.

[21] Appl. No.: 202,546

[22] Filed: Nov. 26, 1971

Related U.S. Application Data

[63] Continuation-in-part of Ser. No. 789,954, Jan. 8, 1969, abandoned.

[51] Int. Cl.² .................................................. C07D 303/34
[52] U.S. Cl. ..................................... 260/348.43; 528/376
[58] Field of Search ......................... 260/348 R, 348.43

[56] References Cited

U.S. PATENT DOCUMENTS

| | | | |
|---|---|---|---|
| 2,731,437 | 1/1956 | Bender et al. | 260/42 |
| 2,965,652 | 12/1960 | Van R. Gaertner | 260/348.6 |
| 3,454,539 | 7/1969 | Greenlee | 260/348 R |

Primary Examiner—Norma S. Milestone
Attorney, Agent, or Firm—Glwynn R. Baker

[57] ABSTRACT

New compounds of the structure

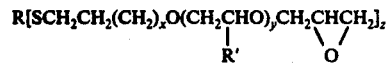

where R is an aromatic, alicyclic or aliphatic group of at least 2 C atoms and up to 18 C atoms, $x$ is an integer from 1 to 9, R' is H, a lower alkyl grup of 1-4 C atoms or —$CH_2Cl$, $y$ is an integer of from 0–10 and $z$ is an integer of from 2 to 6 are prepared by reacting a polythioetherpolythiol with an olefinically unsaturated epoxide or by dehydrohalogenating the corresponding halohydrins. The new compounds are useful as diluents for epoxy resins to reduce their viscosity and to improve flexibility of the cured resins.

12 Claims, No Drawings

POLYTHIOETHERALKYLENEOXIDE EPOXIDES

CROSS-REFERENCE TO RELATED APPLICATION

The present application is a continuation-in-part of my previous application Ser. No. 789,954 filed Jan. 8, 1969, and now abandoned.

SUMMARY OF THE INVENTION

This invention relates to new compounds of the structure

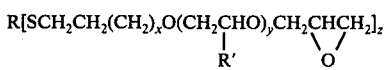

where R is an aromatic group, an alicyclic group or an open chain saturated aliphatic group of at least 8 C atoms, x is an integer of from 1 to 9, R' is H, a lower alkyl group of from 1 to 4 C atoms, or a lower haloalkyl group of from 1 to 4 C atoms, Y is an integer of from 0 to 10 and z is an integer of from 2 to 6, and to methods of preparing the new compounds by dehydrohalogenating the corresponding halohydrin with a hydrogen halide acceptor or by reacting the polythiol with an unsaturated monoepoxide.

Polyglycidyl ethers having a functionality of two or more are difficult to obtain. They usually have been made by reacting a polyalkylene glycol with epichlorohydrin and subsequently ring closing. The reaction between the hydroxyl group of the polyalkylene glycol and epichlorohydrin is usually only partially complete, so that a relatively high proportion of monoepoxy product results.

One of the advantages of this invention is that polyepoxide formation is essentially complete. Another advantage is the average number of epoxide groups can be controlled so that from 2 to 4 such groups can be obtained per molecule. Another advantage is that the physical properties of the final polyepoxide can be varied over a wide range by controlling the values of x, y and the R and R' groups in the generic formula. Another advantage is that the final polyepoxides have structures which are stable to hydrolysis under either acid or alkaline conditions and the most reactive portions of the molecule are the epoxide groups. A further advantage is that the polythioether polyepoxides are of low viscosity and are therefore useful as reactive diluents for polyepoxides such as the diglycidyl ethers of bisphenol A or the glycidyl ethers of phenol-formaldehyde novalacs such as DEN-431 or 438 (products of The Dow Chemical Co.). When copolymerized with these epoxides, tough, impact-resistant polymers are obtained.

DETAILED DESCRIPTION OF THE INVENTION

The precursor halohydrins, used for making the polythioetherpolyepoxides of this invention are prepared by reacting a polymercaptan (i.e. any mercaptan having 2 or more —SH groups) with an olefinically unsaturated ether halohydrin, preferably terminally monoolefinically unsaturated, to thereby form an adduct in which at least two of the —SH groups on the polymercaptan will each add across an olefinically unsaturated portion of the ether halohydrin. The product resulting from such addition will contain at least two halohydrin groups in which the halogen and OH groups are vicinal to each other on individual carbon chains.

Representative halohydrins include: 1-allyloxy-3-chloro-2-propanol, 1-(10-undecenyl)oxy-3-chloro-2-propanol, 1-(2-allyloxy)ethoxy-3-chloro-2-propanol,

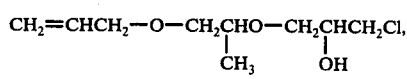

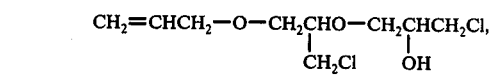

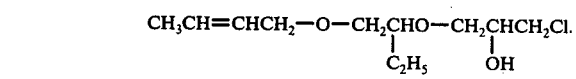

Representative olefinically unsaturated monoepoxides which can be reacted with the polythiols include: allyl glycidyl ether, (2-allyloxy)ethyl glycidyl ether, 4-butenyl glycidyl ether,

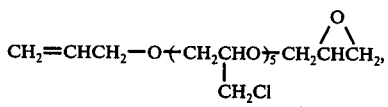

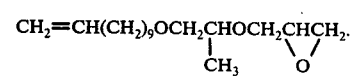

The polythiol can be an aliphatic, oxaalkyl, polyoxaalkyl, thiaalkyl or polythiaalkyl group containing from 2 to 12 carbon atoms, with the provision that the thiol groups are separated by at least two carbon atoms. Examples of suitable polythiols include 1,2-ethanedithiol, 1,3-propanedithiol, bis(2-mercaptoethyl)ether, bis(2-mercaptoethyl)sulfide, 1,8-dimercapto-3,6-dithiaoctane, 1,11-dimercapto-3,9-dithia-6-oxaundecane, bis(3-mercaptopropyl)ether, or 1,8-dimercaptooctane.

The polythiol may be a cycloaliphatic polythiol containing from 6-12 carbon atoms. Suitable polythiols include ethylcyclohexyl dimercaptan (the reaction product of 4-vinylcyclohexene with hydrogen sulfide), dipentene dimercaptan, 1,4-dimercaptocyclohexane, or 1,2,4-tris(2-mercaptoethyl)cyclohexane.

Suitable aryl or aralkyl polythiols include α,α'-dimercapto-p-xylene, 1,3-benzenedithiol, o,p,p'-tris(mercaptomethyl)diphenyl ether.

A final class of polythiols which can be employed are disclosed in my application entitled "Polyetherpolythiols, Method of Preparation and Mixtures of Polythioetherpolythiols with Epoxide Resins", Ser. No. 771,648, filed Oct. 29, 1968, and now abandoned. Typical polyetherpolythiols can be prepared by reacting 1,2-ethanedithiol with a trivinyl cyclohexane, a representative of which is 1,2,4-trivinylcyclohexane; 1,2-ethanedithiol with 1-allyloxy-2-allylbenzene or other allyloxy allylbenzenes; 1,3-propanedithiol with 1-allyloxy-2,6-diallylbenzene or isomers thereof; 1,2-propanedithiol with the triallyl ether of glycerol or 1,2-ethanedithiol with a polyallyl ether of pentaerythritol containing about 3-4 allyl groups and particularly about 3.5 allyl groups.

The proportions of reactants should be such that at least one thiol group is available for each unsaturated carbon to carbon bond. Preferably the unsaturated compound is added to a mixture of the polythiol and catalyst.

The reaction of the dithiol with a compound having 3 to 5 olefinically unsaturated linkages or a mixture of at least one of said compounds with a diolefinically unsaturated compound is preferably carried out in the presence of a free-radical initiating catalyst such as organic peroxides or hydroperoxides, examples of which are benzoyl peroxide or t-butyl hydroperoxide, the azonitriles, such as azoisobutyronitrile, ultra-violet light or a cobalt 60 source of gamma radiation. The resulting polythioether polyols have a thiol functionality greater than 2.05 and usually 2.2 to 4. Thus, the R of the generic formula can be an alkylene group of from 2 to 12 C atoms, an alkylene ether group of 4–12 C atoms, an alkylene thioether group of 4–12 C atoms, an alkylene ether-alkylene thioether group of from 6 to 18 C atoms, a polyalkylene ether or polyalkylenethioether group of 6–18 C atoms, an aromatic hydrocarbon group containing 1–3 rings, an alkylene aromatic group having from 1 to 4 alkylene or oxaalkylene groups each containing 1 to 4 C atoms, polyalkylene diphenyl oxide groups having 2 to 4 alkylene groups of from 1 to 4 C atoms, and the reaction products of a dithiol and a poly-unsaturated compound having at least three carbon to carbon double bonds and mixtures thereof with a diene. These reaction products can contain up to about 50 C atoms.

Catalysis can be effected by any known free radical catalysts which form free radicals at temperatures of 25° to 150°. Also, actinic free radical formers such as U.V. light or gamma rays can be used as catalysts. Typical catalysts include: azobisisobutyronitrile, ditertiarybutyl peroxide, t-butylhydroperoxide, methyl ethyl ketone peroxide, 1-azocyclohexane carbonitrile, t-butyl perbenzoate, benzoyl peroxide and the like.

The reaction can be carried out at a temperature of 25° to about 125° with the unsaturated epoxides and 25° to 150° with the unsaturated halohydrins. Dehydrohalogenation of the halohydrins can be effected with any hydrohalide acceptor such as any of the alkali metal hydroxides preferably NaOH or KOH, or the corresponding carbonates or bicarbonates or tertiary amines such as trimethyl, triethyl or tripropyl amines, or any quaternary ammonium hydroxide. The alkaline alkali metal compounds can be solids or in solution.

Pressure has no effect on the reaction, so that it can be run at atmospheric, superimposed or subatmospheric pressure. Preferred is the autogenous pressure at the reaction temperature employed.

The examples below are intended to illustrate, but not to limit, the invention. In all instances parts are given by weight unless otherwise indicated.

EXAMPLE I

A polythioetherpolythiol was prepared by adding 81.2 g. of 1,2,4-trivinylcyclohexane over a 1½ hour period to 283 g. of 1,2-ethanedithiol containing 1 g. of azoisobutyronitrile. The mixture was stirred for an additional 4 hours. A temperature of 70° C was maintained during the entire period. Unreacted 1,2-ethanedithiol was removed by distillation at a pressure of 0.5 mm. A yield of 201 g. of a polythioetherpolythiol having a viscosity of 1300 cps. was recovered. The polythioetherpolythiol analyzed 40.9% by weight total sulfur and 16.9% as SH.

The reaction mixture contained an appreciable amount of the triadduct

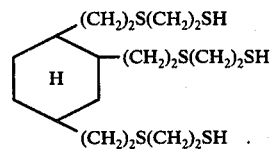

A solution of 112 g. of the above polythioetherpolythiol and 1 g. of azoisobutyronitrile in a 500 ml. flask was heated to 70° C and 240 g. of allyl glycidyl ether were added dropwise during a two hour period. The mixture was then heated at 70° C for an additional 7 hours. Unreacted allyl glycidyl ether was removed by distilling to 70° at 1.0 mm., leaving 187 g. of a yellow epoxide having a viscosity of about 1300 cps. and an epoxide equivalent weight of 292. An infrared spectrum showed that hydroxyl and olefinically unsaturated groups were absent.

EXAMPLE II

A series of runs was made using polythioetherpolythiols, which were made by reacting 1,2-ethane dithiol with 1 allyloxy-2,6-diallyl benzene, 1-allyloxy-2-allyl benzene, a mixture containing 50/50 mol percent of the diallyl ether of bisphenol A and triallyloxy propane. The polyepoxide in each case was prepared by placing the polythioetherpolythiol in a 50 ml. high silica glass tube and adding allyl glycidyl ether dropwise. The mixture was irradiated with a UA-2 lamp during the entire run of 2 hours each. The reaction was effected while bubbling a stream of nitrogen through the mixture. Tablulated below are the data from the several runs. In the table AGE means allyl glycidyl ether.

TABLE I

| Run No. | Polythiol Prepared From: Olefin | HSCH$_2$CH$_2$SH/ Olefin Ratio | —SH eq. wt. | g. Polythiol | g. AGE | g. Product | Viscosity | Epoxide eq. wt. |
|---|---|---|---|---|---|---|---|---|
| 1 | CH$_2$CH=CH$_2$ / O—CH$_2$CH=CH$_2$ / CH$_2$CH=CH$_2$ (471-9-72) | 6 moles/1.0 mole | 206 | 20.6 | 11.4 | 30 | 10.7 poises | 362.3 |

TABLE I-continued

| Run No. | Polythiol Prepared From: Olefin | HSCH₂CH₂SH/ Olefin Ratio | —SH eq. wt. | g. Polythiol | g. AGE | g. Product | Viscosity | Epoxide eq. wt. |
|---|---|---|---|---|---|---|---|---|
| 2 | ⟨benzene ring⟩—OCH₂CH=CH₂ <br> CH₂CH=CH₂ <br> (471-10-3) | 5.0 moles/1.25 moles | 197 | 19.7 | 11.4 | 30.4 | ~1.85 | 326.4 |
| 3 | Me₂C⟨benzene⟩(—O—CH₂CH=CH₂)₂ <br> + <br> CH₂—O—CH₂CH=CH₂ <br> CH—O—CH₂CH=CH₂ <br> CH₂—O—CH₂CH=CH₂ <br> 50/50 mole % <br> (471-9-34) | 5 moles/1.0 mole | 228 | 22.8 | 11.4 | 33 | ~3.30 | 362.3 |
| 4 | Me₂C⟨benzene⟩(—OCH₂CH=CH₂)₂ <br> CH₂CH=CH₂ <br> CH₂—O—CH₂CH=CH₂ <br> CH—O—CH₂CH=CH₂ <br> CH₂—O—CH₂CH=CH₂ <br> 50/50 mole % <br> (471-9-36) | 4 moles/0.66 mole | 231 | 23.1 | 11.4 | 33.2 |  | 391.4 |

The polyepoxide was prepared by placing the polythiol in a 50 ml. Vycor tube and adding the AGE portionwise. The mixture was then irradiated with a UA-2 lamp under a stream of $N_2$ for 8 hours.

EXAMPLE III

A mixture of 4 g. azobisisobutyronitrile and 150 g. of 1-allyloxy-3-chloro-2-propanol was heated to 70°–73° C while adding 59 g. of 2,2'-bis(mercaptoethyl) ether. After a few hours post reaction, the product was cooled to room temperature. Then 50 g. of NaOH pellets were added while maintaining the temperature below 40° C. The mixture was stirred for 2 hours and then filtered to yield a yellow, free flowing polyepoxide.

This procedure was repeated with 77 g. of 2,2'-bis(mercaptoethyl)sulfide and 150 g. of 1-allyloxy-3-chloro-2-propanol, the mixture was diluted with 200 ml. benzene before adding the 50 g. of NaOH pellets. Stirring was continued for 5 hours after adding the NaOH. Sufficient water was added to the mixture to dissolve the NaCl and the benzene layer was separated from the aqueous layer. Evaporation of the solvent left a yellow fluid epoxide with an epoxide equivalent weight of 254.

EXAMPLE IV

Certain dithiols were reacted with unsaturated alkylene ether chlorohydrins. In each instance the dithiol was added to a chlorohydrin and was contained in a 600 ml. beaker and stirred with a magnetic stirrer. The contents were irradiated with a UV-2 ultra violet lamp for four hours. During the entire period the beaker was cooled with tap water. The molar ratio of the chlorohydrin to the dithiol was at least 2 to 1. After completion of the reaction sufficient solid NaOH was added to the mixture to convert the dihalohydrin to a diepoxide. It is to be understood that the main product formed in each instance was the diadduct of the unsaturated halohydrin to the dithiol.

Tablulated below are the list of products reacted and the epoxide equivalent weight of the diepoxide formed.

TABLE II

| Dithiol | Chlorohydrin | Epoxide eq. wt. |
|---|---|---|
| ⟨cyclohexane with CH₃, SH, H substituents and CH₃—C(H)—CH₂SH group⟩ | CH₂=CHCH₂OC₂H₄OCH₂CHOHCH₂Cl | 487 |
| HS(CH₂)₈SH | CH₂=CH(CH₂)₉OCH₂CHOHCH₂Cl | 476 |

The polyepoxides of this invention are, in general, low to medium viscosity liquids which can be used as reactive diluents for bisphenol A type diepoxides.

The epoxides of this invention can be polymerized by strong bases or tertiary amines such as benzyldimethylamine, tetramethylguanidine, and the like. The epoxides are particularly useful as impact modifiers for bisphenol A based epoxies which are well known items of commerce.

Other polythioether polyepoxides of this invention can be blended with 10–30 to about 40% by weight of known liquid epoxide resins or novolacs and subsequently cured with nitrogen containing curing agents to provide solvent or impact resistant, flexible products.

To demonstrate the ability of the polyepoxidepolythioethers for improving the impact properties of commercially available bisphenol A based epoxy resin, several of the products of the examples were copolymerized with a liquid, diglycidyl ether resin of bisphenol A. The liquid resin had an epoxide equivalent weight of 172–178 and a viscosity at 25° C of 40–64 poise. One such resin is designated as DER$^R$332 by The Dow Chemical Company. A ten gram sample of each mixture described below was thoroughly blended with 0.5 gram of benzyldimethylamine and heated in an aluminum cup for 17 hours at 100° C.

| DER$^R$332 % by weight | Product of Example No. | % by Weight |
|---|---|---|
| 50 | 1 | 50 |
| 70 | II, Run 1 | 30 |
| 70 | II, Run 2 | 30 |
| 70 | II, Run 3 | 30 |
| 100 | — | — |

All the samples gave rigid solids which adhered well to the aluminum cup. When the sample containing the liquid resin of the diglycidyl ether of bisphenol A was struck with a hammer, it shattered into numerous pieces. The samples which contained the polyepoxide polythioethers of the examples withstood repeated pounding with the ball-peen of a hammer.

The remaining products of the generic formula

when blended with the liquid resin of diglycidyl ethers of bisphenol A and copolymerized also form tough, shock resistant solid resins, which adhere well to aluminum and other metals.

The copolymers as above described, are useful for adhering metal to metal, metal to glass, metal to fibers, both cellulosic and the well-known synthetic fibers. They are also useful as solvent resistant flexible coatings for protecting metal sheet and formed articles.

I claim:

1. Compounds of the structure

wherein $x$ is an integer from 1 to 9, R' is H, an alkyl group of from 1 to 4 C atoms or CH$_2$Cl, $y$ is an integer from 0 to 10, $z$ is an integer from 2 to 3 and R is —(CH$_2$)$_2$O(CH$_2$)$_2$, —(CH$_2$)$_3$O(CH$_2$)$_3$—, —(CH$_2$)$_2$S(CH$_2$)$_2$—, —(CH$_2$)$_2$S(CH$_2$)$_2$S(CH$_2$)$_2$—, —(CH$_2$)$_2$S(CH$_2$)$_2$O(CH$_2$)$_2$S(CH$_2$)$_2$—,

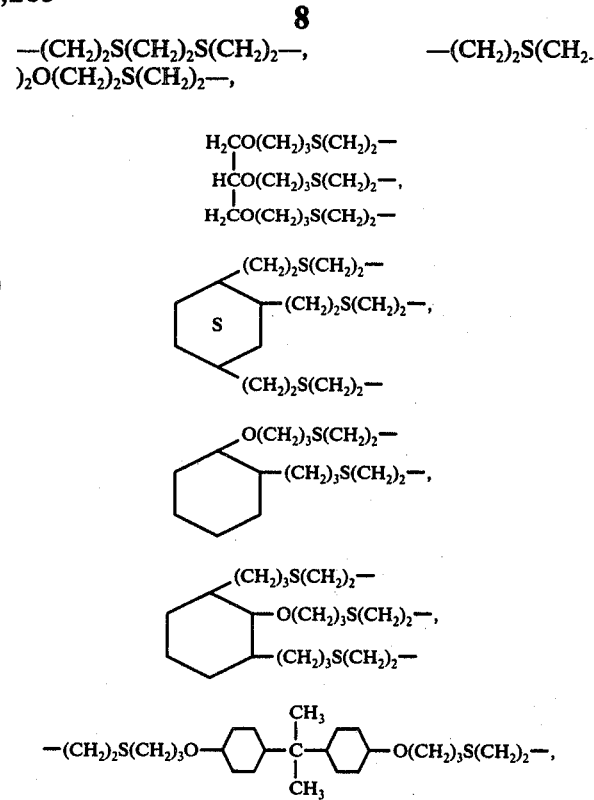

or the reaction product of a polyallyl ether of penterythritol having an average of about 3.5 allyl groups and 1,2-ethanedithiol.

2. Compounds of claim 1 in which R is

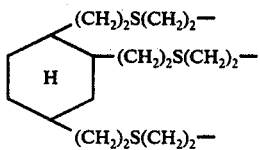

$x$ is 1 and $y$ is 0 and $z$ is 3.

3. Compounds of claim 1 in which R is

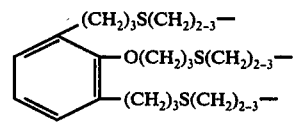

4. Compounds of claim 1 in which R is

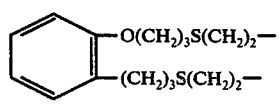

5. Compounds of claim 1 in which R is

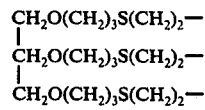

6. Compounds of claim 1 in which R is

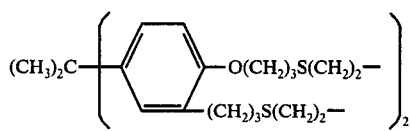
7. Compounds of claim 1 in which R is —(CH$_2$)$_2$S(CH$_2$)$_2$—.
8. Compounds of claim 3 in which $x$ is 1 and $y$ is 0.
9. Compounds of claim 4 in which $x$ is 1 and $y$ is 0.
10. Compounds of claim 5 in which $x$ is 1 and $y$ is 0.
11. Compounds of claim 6 in which $x$ is 1 and $y$ is 0.
12. Compounds of claim 3 in which $x$ is 1, R' is H and $y$ is 0.
* * * * *